United States Patent [19]

Hedengren et al.

[11] Patent Number: 5,006,800
[45] Date of Patent: Apr. 9, 1991

[54] EDDY CURRENT IMAGING APPARATUS AND METHOD USING PHASE DIFFERENCE DETECTION

[75] Inventors: Kristina H. V. Hedengren; Donna C. Hurley, both of Schenectady; John D. Young, Rexford, all of N.Y.

[73] Assignee: General Electric Company, Schenectady, N.Y.

[21] Appl. No.: 431,791

[22] Filed: Nov. 6, 1989

[51] Int. Cl.⁵ .................... G01R 33/12; G01N 27/82
[52] U.S. Cl. .................................. 324/233; 324/237; 324/238
[58] Field of Search ............... 324/233, 234, 236–243, 324/225

[56] References Cited

U.S. PATENT DOCUMENTS 4,594,549 6/1986 Smith et al. ...................... 324/233
4,823,082 7/1989 Nasu et al. ....................... 324/233

OTHER PUBLICATIONS

K. H. Hendengren et al., "Use of Imaging Techniques For Eddy Current NDE", From Review of Progress in Quantitative Nondestructive Evaluation, vol. 7A, Plenum Pub. Corp., May 1988, pp. 357–365.

Primary Examiner—Walter E. Snow
Attorney, Agent, or Firm—Marilyn Glaubensklee; James C. Davis, Jr.; Paul R. Webb, II

[57] ABSTRACT

A phase-difference eddy current imaging system has a bridge circuit including a pair of coils with one or both coils disposed proximate an object that may contain one or more flaws. An oscillator is coupled to the bridge circuit and also to a pair of phase detectors that are coupled to the coils. A differential amplifier is coupled to the phase detectors for providing a comparison signal. A method for eddy current imaging using phase difference detection comprises providing relative movement between an object and at least one of a pair of coils, measuring the phase of the effective reactance in each of the coils, comparing the measured values, and formatting the compared values as a function of spatial position.

18 Claims, 2 Drawing Sheets

EDDY CURRENT IMAGING APPARATUS AND METHOD USING PHASE DIFFERENCE DETECTION

BACKGROUND OF THE INVENTION

The present invention relates to eddy current imaging of defects in materials, and, more particularly, to using phase difference to determine the depth of defects.

In the prior art of FIG. 1, eddy current probes contain two coils 14a and 14b that are simultaneously excited from an oscillator 16 through a bridge circuit 10 having resistors 12a and 12b. The probe is disposed near a material to be examined for defects. The probe coils may be arranged so that both lie in a plane parallel to the material (differential geometry) or so that one lies near the material and the other serves as a reference (absolute geometry). Although only the differential-probe geometry is discussed here, the same principles apply to the absolute-probe geometry. The received signal, that is, the voltage across the coils, is mixed in mixer 30b with the excitation signal phase-shifted by 90 degrees to produce the quadrature (Q) signal component. Likewise, the received signal is mixed in mixer 30a with the excitation signal directly (i.e., phase-shifted by 0 degrees) to form the in-phase (I) signal component. The signals from mixers 30a and 30b are then respectively passed through filters 31a and 31b and then respectively through amplifiers 32a and 32b. Filters 31a and 31b may be low-pass (typical cut off frequency, 100 Hz), high-pass (typical cut off frequency, 5 Hz), or a combination of the two, i.e., a bandpass filter. The output signals from amplifiers 32a and 32b are then each applied to rotation circuits 33. Circuit 33a forms a signal $H = I \cos(\theta) - Q \sin(\theta)$, while circuit 33b forms a signal $V = I \sin(\theta) + Q \cos(\theta)$, wherein $\theta$ is a desired rotation angle represented by a DC input control voltage to circuits 33, which have ROM look up tables to generate $\sin \theta$ and $\cos \theta$, and H and V respectively stand for horizontal and vertical axis. Thus each of circuits 33 can additionally comprise a pair of multiplier circuits, each of which receives the I or Q signals and also the $\theta$ signal, with the outputs of the multipliers in respective rotation circuits 33 being added together.

The coils are scanned manually or mechanically over the material to be examined. In the vicinity of a defect, a change in the H and V signals occurs. One of these signal components (V in FIG. 1) is then passed through a threshold circuit 34, such as a differential amplifier, having a predetermined threshold amplitude as determined by a potentiometer 35, for defect detection. The signal from threshold circuit 34 can be applied to an alarm (not shown). Defect measurements are possible with this technique for a minimum defect length of about 10 to 15 mils (0.254 to 0.381 mm). By defect "length" is meant the larger of the two defect dimensions parallel to the scanned surface of a plate material (not shown in FIG. 1). If desired, circuit 33a can be eliminated.

With the prior art, defect depth (the dimension perpendicular to the scanned surface) cannot be directly measured. A means to quantitatively characterize defect depth makes it possible to distinguish between defects and small surface dents or scratches, thus determining the true material quality. Therefore a depth sizing technique is of immediate potential benefit.

It is therefore an object of the invention to determine the depth of surface-breaking defects.

SUMMARY OF THE INVENTION

Apparatus in accordance with the invention for phase-difference eddy current imaging of an object comprises a pair of impedance elements adapted to be disposed proximate the object; means for causing relative motion between the object and said elements; an oscillator coupled to said elements; a pair of phase detectors coupled to said oscillator and said elements, said oscillator providing signals having the same phase to both of said phase detectors and means for comparing the output signals from said phase detectors.

A method in accordance with the invention for phase-difference eddy current imaging of an object comprises providing relative movement between the object and at least one of a pair of coils; measuring the effective reactance in each of said coils; and comparing the measured reactance changes.

BRIEF DESCRIPTION OF THE DRAWING

In the drawing, corresponding reference numerals are applied to corresponding elements.

DETAILED DESCRIPTION

Figure 1:
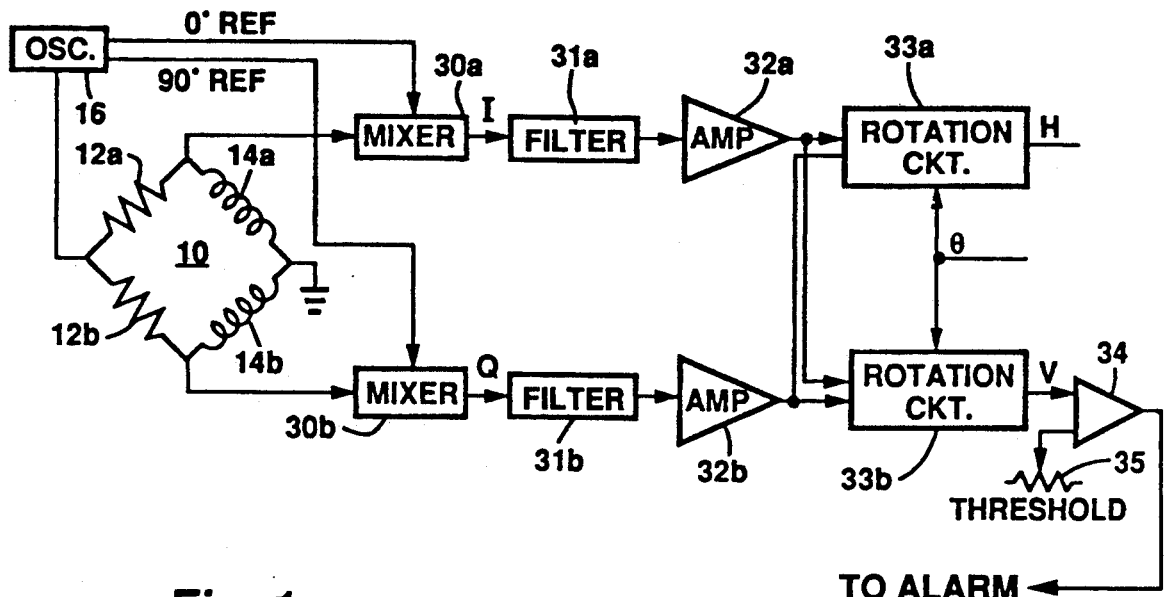
FIG. 1 is a partly schematic and partly block diagram of the prior art.
Figure 2:
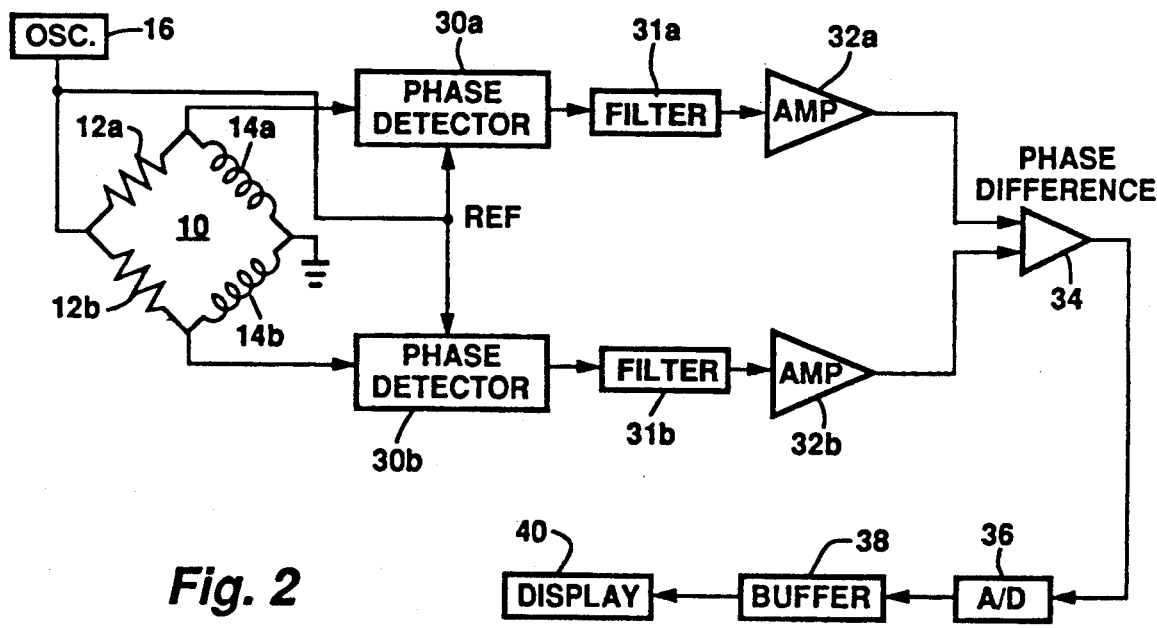
FIG. 2 is a partly schematic and partly block diagram of an embodiment of the invention.

FIG. 2 shows the basic detection circuitry components. A balanced impedance bridge 10 comprises a pair of impedance elements, such as resistors or inductors 12a and 12b, and a pair of impedance elements such as probe coils 14a and 14b. Typically, if impedance elements 12 are resistors, they have a resistance of about 150 ohms, while coils 14 have a reactance of about 150 ohms at the excitation frequency although other values can be used for both impedance elements 12 and coils 14. However, for the bridge 10 to be balanced, the impedance elements 12 must have equal resistance or reactance value and the coils 14 must have equal inductance. The junction of coils 14 is coupled to a reference voltage such as ground. The junction of impedance elements 12 is driven by an AC excitation signal from oscillator 16, which typically has a frequency between about 0.1 to 10 MHz. Several frequencies can be used although only one at a time.

Figure 3:
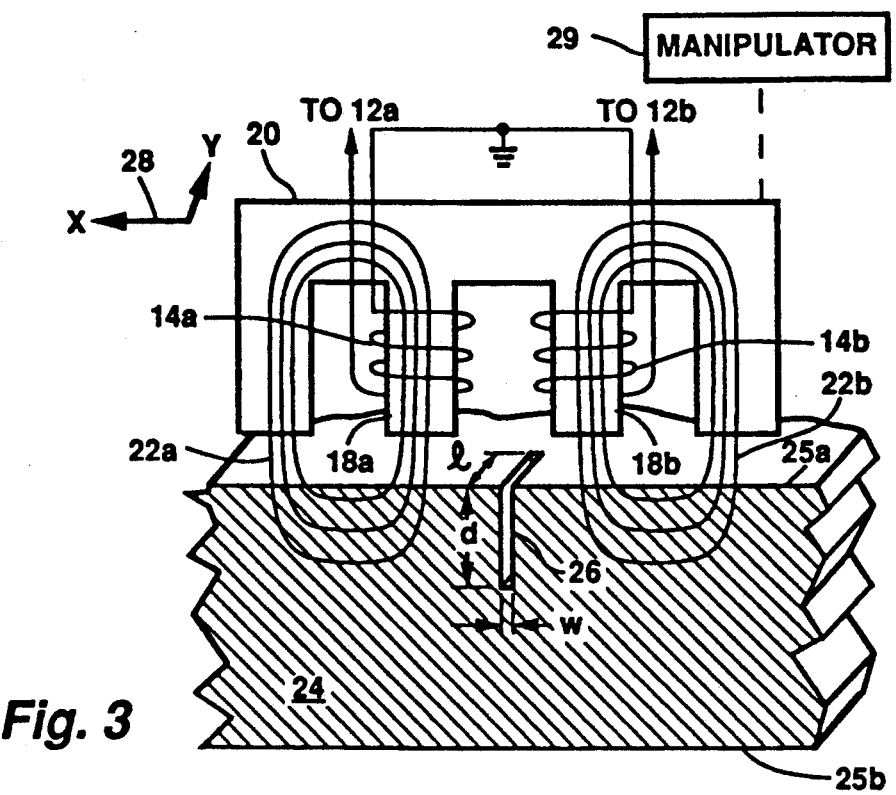
FIG. 3 is a perspective view of an object having a defect and a differential-coil probe.

FIG. 3 shows coils 14a and 14b respectively disposed on ferrite cores 18a and 18b of a ferrite cup-shaped coil form 20. A differential-coil geometry is shown in FIG. 2, but the same discussion can be applied to an absolute-coil geometry. While coils 14 are shown wound in opposite directions, they can be wound in the same direction. Cores 18 are "D-shaped" when seen in a bottom cross-sectional view, while cup 20 is circular in a cross-section and typically has a diameter of 0.060 inches (1.524 mm). Coils 14a and 14b respectively produce flux lines 22a and 22b, which create eddy currents in nearby objects of conducting materials, such as metal plate 24. Plate 24 has major surfaces 25a and 25b and a flaw 26, which has dimensions of length "l" and width "w"

parallel to, and a depth "d" perpendicular to, the major surface 25a. Typically, the thickness of plate 24 (the distance between surfaces 25a and 25b) is between ½ to 3 inches (1.27 to 7.62 cm). A conventional X-Y manipulator 29 linearly moves cup 20 in the direction "X" indicated by arrow 28. If desired, manipulator 29 can then increment cup 20 by one unit in the "Y" direction and again move cup 20 in the "X" direction. This is repeated until a two dimensional scan is complete. Alternatively, the plate 24 can be moved, while cup 20 is stationary since this also provides relative motion therebetween. However, since plate 24 is normally much heavier than enclosure 20, this is normally not done. If manipulator 20 is a conventional rotary manipulator, cup 20 can be rotationally turned for purpose of detecting flaws in holes, in which case cup 20 would be positioned perpendicular to the axis of the rotation. It will be appreciated that coil form 20 need not be cup-shaped and object 24 can have a shape other than a plate.

The signals from coils 14a and 14b are respectively applied to phase detectors 30a and 30b, such as the four diode bridge type RAY-6 made by Mini Circuits Co. Inc., Brooklyn, N.Y. The phase detectors 30 are actually mixing circuits. In practice, the excitation reference signal from oscillator 16 is applied with sufficient amplitude to saturate the mixer diodes, so that the mixer acts as a phase detector. The output signals from the phase detectors 30a and 30b represent the phase of the signals from coils 14a and 14b, respectively, relative to the oscillation signal. After being respectively filtered by filters 31a and 31b. Typically comprising bandpass filters with a passband between about 5 Hz to about 100 Hz, and respectively amplified by amplifiers 32a and 32b, the phase-representative signals are then compared using a differential amplifier 34. This produces a single output signal in accordance with the relative phase difference between the signals from coils 14a and 14b. The output signal from amplifier 34 is digitized by analog-to-digital converter 36. The digitization process is repeated for either a one or two-dimensional grid of positions in accordance with the scan performed by manipulator 29. These results can be processed to minimize effects due to the specific system configuration, e.g., subtracting the signal from a defect-free object to enhance contrast. The data are displayed as a phase image using display 40 (e.g., a video monitor), corresponding to phase difference versus position at a specific oscillator frequency. If the phase differences at several frequencies have been acquired, the maximum difference for each position independent of frequency can also be displayed.

When cup 20 is not near a flaw, bridge 10 is balanced and thus equal signals are provided to differential amplifier 34. Therefore the output of differential amplifier 34 is zero, and display 40 shows a value of zero. When one of the coils 14 is in the vicinity of flaw 26, it will undergo a change in inductance, and therefore reactance, due to a change in the eddy currents, resulting in a change in voltage across the coil. In particular, since cup 20 is linearly moving as indicated by arrow 28, a voltage change is induced in coil 14a as it approaches the defect, and the phase difference between opposite sides of the bridge will be nonzero. Then, a voltage change in coil 14b is induced as it passes over the defect, and the phase difference will be of equal magnitude but opposite sign. As the probe is scanned across a defect, the output of differential amplifier 34 will change from zero, to a large positive, to a large negative, to zero value. The output signal from amplifier 34 is applied to an analog-to-digital converter 36. The digital signals from converter 36 are applied to a buffer 38, which can be read out after the scan is complete. Therefore, a two dimensional spatial image format of the scanned object with the defect amplitude indicated by color or gray scale can be displayed by a display 40.

Figure 4:
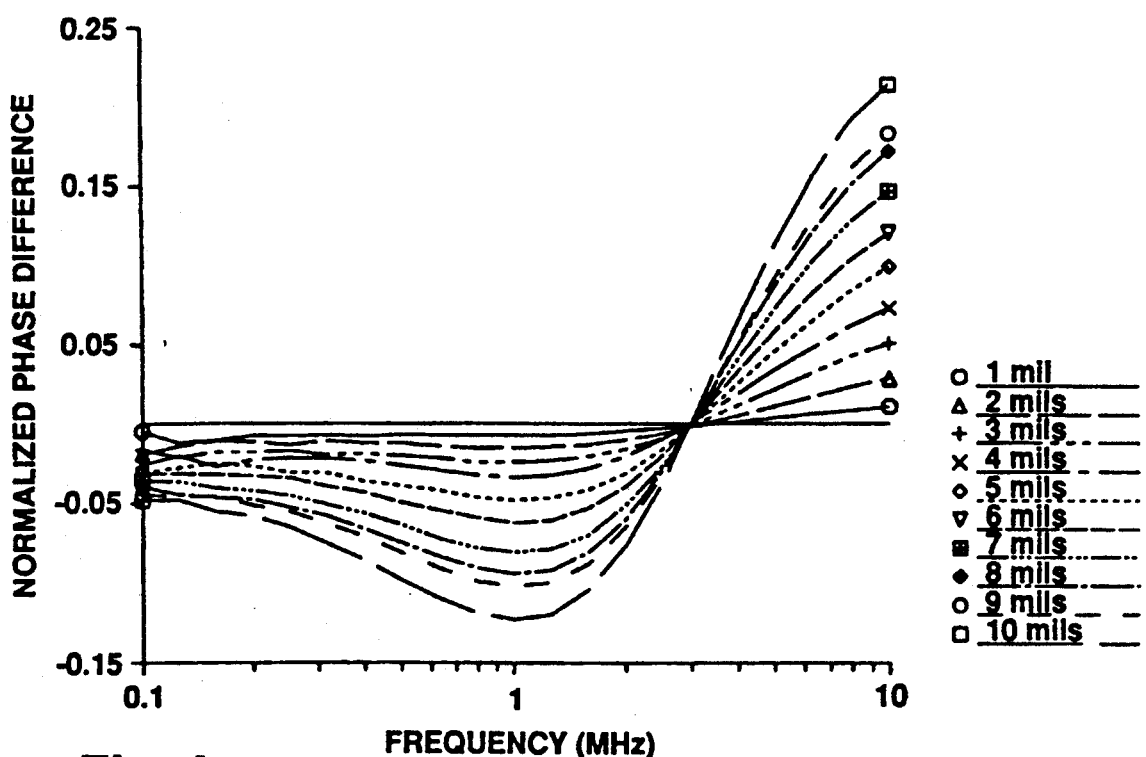
FIG. 4 is a graph of phase difference verses frequency for various defect depths, obtained with a differential-coil probe and normalized to the probe response for a region free of defects.

Results of phase-difference detection are shown in FIG. 4. The curves in the figure correspond to the difference in phase angle in degrees between coils 14 as a function of the frequency of the signal from oscillator 16 for ten electrode discharge machined (EDM) slots of varying depth in a nickel alloy plate, such as type "Inconel 718" made by International Nickel Co. Inc., N.Y., N.Y., with depths ranging from 1 to 10 mils (0.0254 to 0.254 mm) and length 500 mils (1.27 cm). Each curve represents the probe response when one coil is situated approximately directly above the center of each defect slot. These curves have been normalized by subtracting data which represent the response of the same probe for a defect-free area of the same material. It is believed that the specific frequencies at which the curves are most widely separated (near 1 MHz and 10 MHz in FIG. 4) and the frequency at which the curves cross (near 3 MHz) may be attributed to the particular impedance of bridge 10 and the length of cables (not shown) between bridge 10 and phase detectors 30. The roughly linear variation of signal with slot depth shows the effectiveness of using phase-difference signals as a means of obtaining quantitative depth information. In particular, the curves are well separated and distinct from one another, particularly near 1 MHz even for a depth of 1 mil. This compares with a minimum resolvable length of at best 10 mils with the prior art and no direct determination of the defect depth. One would therefore use a frequency of about 1 MHz or about 10 MHz in the implementation of a preferred embodiment of the present invention.

What is claimed is:

1. Apparatus for eddy current imaging using phase difference detection of an object, said apparatus comprising:
    a pair of coils, at least one of said coils being adapted to be disposed proximate to the object;
    means for causing relative motion between the object and said coils;
    an oscillator coupled to said coils for causing said at least one of said coils to create eddy currents in the object;
    a pair of phase detectors coupled to said oscillator and to said coils, said oscillator providing signals having the same phase to both of said phase detectors; and
    means for comparing the output signals from said phase detectors.

2. The apparatus of claim 1 wherein said coils are coupled in a bridge circuit.

3. The apparatus of claim 1 wherein said means for causing relative motion comprises a linear manipulator.

4. The apparatus of claim 1 wherein said means for causing relative motion comprises a rotary manipulator.

5. The apparatus of claim 1 wherein said oscillator has at least one frequency between about 0.1 to 10 MHz.

6. The apparatus of claim 5 wherein said frequency is about 1 MHz.

7. The apparatus of claim 1 wherein said frequency is about 10 MHz.

8. The apparatus of claim 1 wherein said comparing means comprises a differential amplifier.

9. The apparatus of claim 1 further comprising an analog-to-digital converter coupled to said comparing means, a buffer coupled to said converter, and a display means, coupled to said buffer, for displaying two spatial dimensions.

10. The apparatus of claim 1 further comprising a pair of bandpass filters coupled between said phase detectors, respectively, and said comparing means.

11. The apparatus of claim 10 wherein each of said bandpass filters has a band pass of between about 5 Hz to 100 Hz.

12. Apparatus for eddy current imaging using phase difference detection of an object, said apparatus comprising:
  a bridge circuit including a pair of coils, at least one of said coils being adapted to be disposed proximate the object;
  an oscillator coupled to said bridge circuit for causing said at least one of said coils to create an eddy current in the object;
  a pair of phase detectors respectively coupled to said coils, each of said detectors being coupled to said oscillator to receive signals of the same phase; and
  a difference amplifier having a pair of inputs respectively coupled to said detectors.

13. A method for eddy current imaging using phase difference detection of an object, said method comprising:
  supplying signals from an oscillator to a pair of coils, at least one of which creates an eddy current in the object;
  providing relative movement between the object and said at least one of the coils;
  measuring the effective reactance in each of said coils; and
  comparing measured reactance values.

14. The method of claim 13 wherein said providing step comprises linearly moving said coils.

15. The method of claim 13 wherein said providing step comprises rotating said coils.

16. The method of claim 13 wherein said measuring step comprises respectively mixing signals from said coils with reference signals having equal phase.

17. The method of claim 13 wherein said comparing step comprises subtracting the detected reactance values.

18. The method of claim 13 further comprising converting the compared reactance values to a digital signal, storing said digital signal, and displaying the value of said digital signal as a function of spatial position.

* * * * *

UNITED STATES PATENT AND TRADEMARK OFFICE
CERTIFICATE OF CORRECTION

PATENT NO. : 5,006,800

DATED : April 9, 1991

INVENTOR(S) : Kristina H.V. Hedengren, Donna C. Hurley and John D. Young

It is certified that error appears in the above-identified patent and that said Letters Patent is hereby corrected as shown below:

On the title page, in reference to Attorney, Agent, or Firm:

Please change Marilyn Glaubensklee; James C. Davis, Jr; Paul R. Webb, II to:

Paul R. Webb, II; James C. Davis, Jr.

Signed and Sealed this

Eleventh Day of August, 1992

*Attest:*

DOUGLAS B. COMER

*Attesting Officer*  *Acting Commissioner of Patents and Trademarks*